US00PP37739P2

(12) United States Plant Patent
Holtmaat

(10) Patent No.: US PP37,739 P2
(45) Date of Patent: Oct. 6, 2026

(54) ***RUDBECKIA* PLANT NAMED 'RUDBKS772'**

(50) Latin Name: *Rudbeckia hirta*
Varietal Denomination: RUDBKS772

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 19/463,084

(22) Filed: Jan. 29, 2026

(30) Foreign Application Priority Data

Oct. 27, 2025 (QZ) ..... PBR 20252206

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Rudbeckia* plant named 'RUDBKS772' that is characterized by its medium plant size, its early blooming season, and its inflorescences with multi-colored ray florets that are yellow with red towards the base.

2 Drawing Sheets

Botanical classification: *Rudbeckia hirta.*
Variety denomination: 'RUDBKS772'.

CROSS-REFERENCE TO RELATED APPLICATIONS

This application claims priority to European Community Plant Variety Office (CPVO) Plant Breeder's Rights Application No. 2025/2206 filed on Oct. 20, 2025, under 35 U.S.C. 119(f), the entire contents of which is incorporated by reference herein. This application is co-pending with a U.S. Plant Patent Application filed for a plant derived from the same breeding program that is entitled *Rudbeckia* Plant Named 'RUDBSU674' (Co-pending U.S. Plant patent application Ser. No. 19/463,090).

BACKGROUND OF THE INVENTION

The present invention relates to a new and distinct cultivar of *Rudbeckia hirta* and will hereafter by referred to by its cultivar name, 'RUDBKS772'. The new cultivar is an herbaceous perennial grown for use as a landscape plant.

'RUDBKS772' was selected in July of 2022 as a single unique plant by the Inventor from amongst seedlings in a trial field in Zuidwolde, Netherlands. The trial field had been planted with seed derived from open pollination of numerous unpatented and unnamed proprietary plants from the Inventor's breeding program. The collected seeds were pooled before sowing and therefore the parentage is unknown.

Asexual propagation of the new cultivar was first accomplished under the direction of the Inventor by tissue culture using meristematic tissue in Heerhugowaard, The Netherlands in August of 2022. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'RUDBKS772' as a unique cultivar of *Rudbeckia.*

1. 'RUDBKS772' exhibits a medium plant size.
2. 'RUDBKS772' exhibits an early blooming season.
3. 'RUDBKS772' exhibits inflorescences with multi-colored ray florets that are yellow with red towards the base.

'RUDBKS772' can be compared to the *Rudbeckia* cultivars 'RUHT25' (U.S. Plant Pat. No. 30,728) and 'RUDHT53' (U.S. Plant Pat. No. 30,727). 'RUHT25' is similar to 'RUDBKS772' in having multi-colored ray florets. 'RUHT25' differs from 'RUDBKS772' in having a taller plant height and a later blooming season. 'RUDHT53' is similar to 'RUDBKS772' in having an early blooming season and a similar growth habit. 'RUDHT53' differs from 'RUDBKS772' in having more inflorescences and ray florets that are solid yellow in color.

'RUDBKS772' can also be compared to the co-pending cultivar *Rudbeckia* 'RUDBSU674'. 'RUDBSU674' differs from 'RUDBKS772' in having inflorescences with ray florets that are yellow from the tip to the mid-section and dark red from the mid-section to the base.

BRIEF DESCRIPTION OF THE DRAWINGS

The accompanying color photographs illustrate the overall appearance and distinct characteristics of the new *Rudbeckia*. The photographs were taken of a 4-month-old plant of 'RUDBKS772' as grown outdoors in a 19-cm container in Zuidwolde, The Netherlands.

The photograph in FIG. 1 is a side view of 'RUDBKS772' in bloom.

Figure 1:
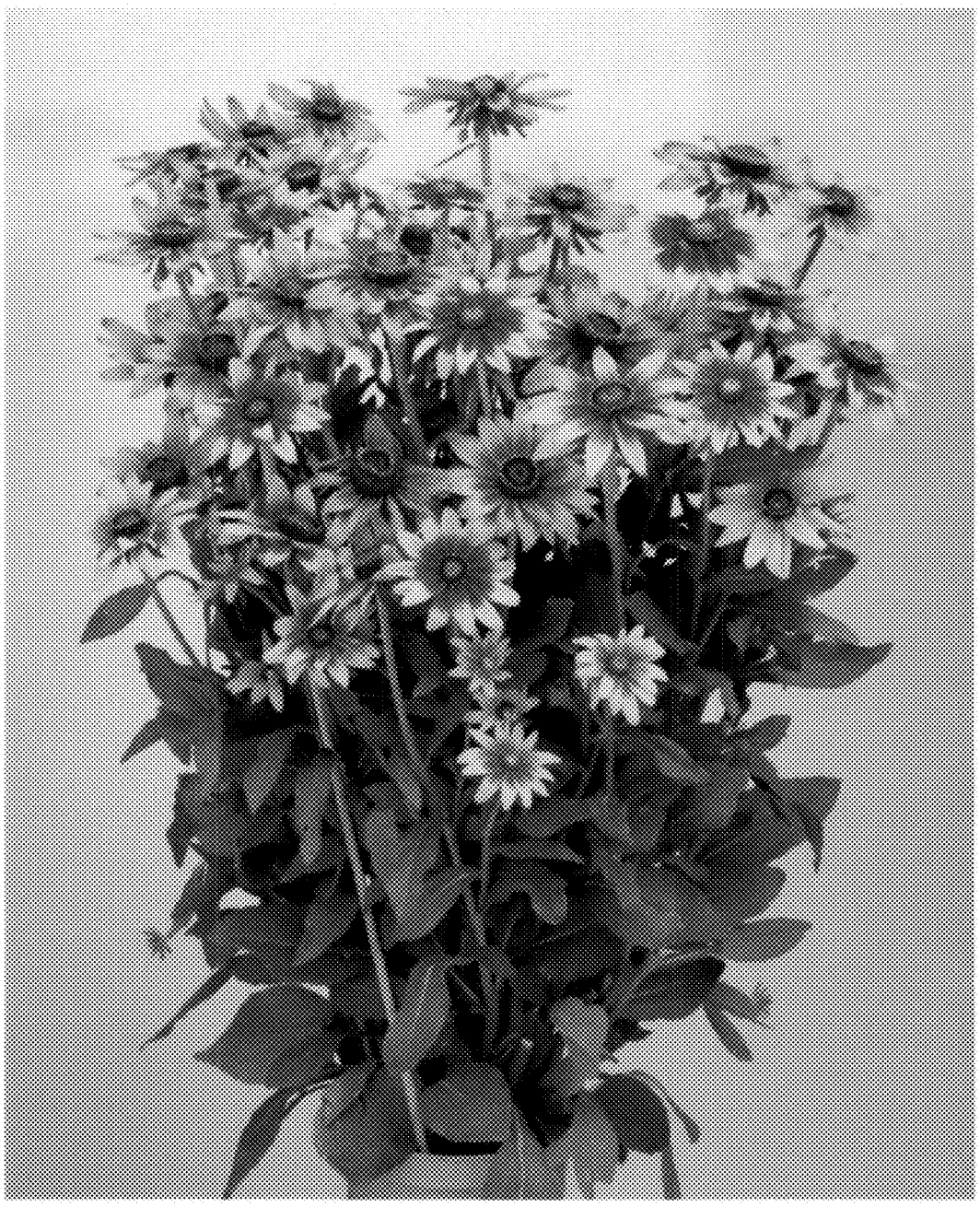
Figure 2:
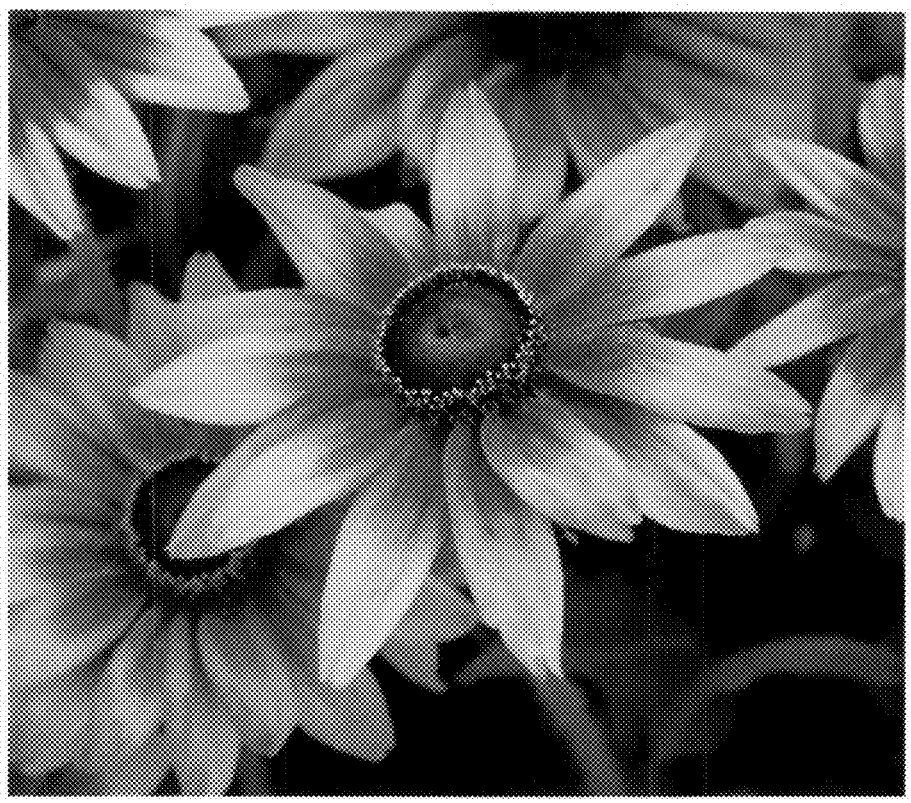

The photograph in FIG. 2 provides a close-up view of an inflorescence of 'RUDBKS772'.

Figure 3:
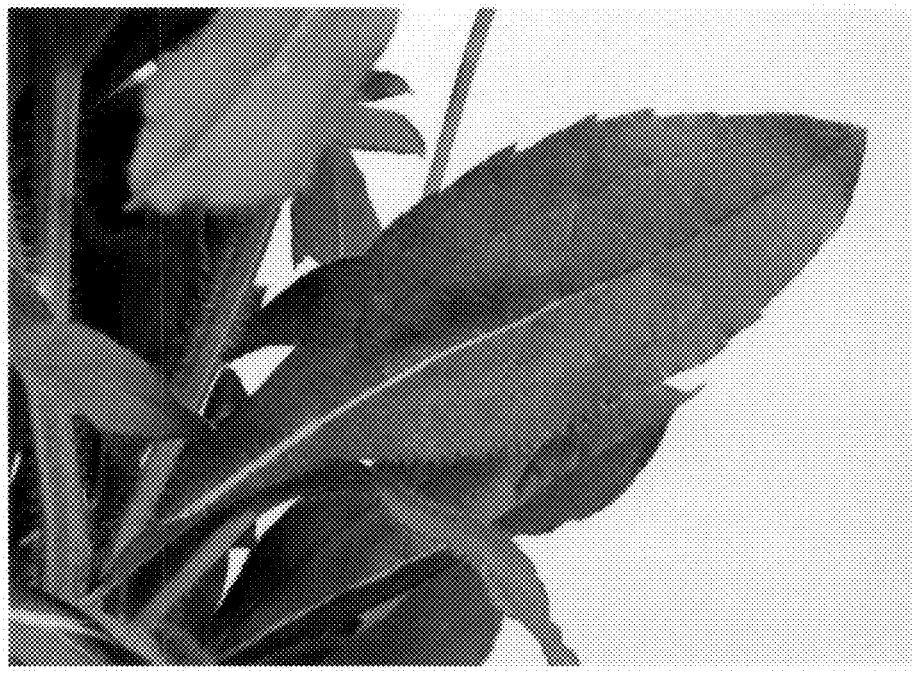

The photograph in FIG. 3 provides a close-up view of a leaf of 'RUDBKS772'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 4-month-old plants of 'RUDBKS772' as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with the 6$^{th}$ edition 2015 (2019 reprint) Colour Chart of The Royal Horticultural Society, London, England, except where general color terms of ordinary dictionary significance are used.

General description:

*Blooming period*.—Early summer to late summer in The Netherlands.

*Plant type*.—Biennial perennial.

*Plant habit*.—Upright, compact.

*Plant shape*.—Broadly obovate.

*Height and spread*.—Average of 60 cm in height from soil level to top of foliar plane and 74.6 cm in height from soil level to top of floral plane, 56.5 cm in diameter as a 4-month-old plant grown in a container.

*Hardiness*.—At least in U.S.D.A. Zones 4 to 10.

*Diseases and pests*.—No susceptibility or resistance to diseases or pests has been observed.

*Root description*.—Fine and fibrous.

*Propagation*.—Tissue culture.

*Root development*.—An average of 4 weeks for root initiation with a fully rooted plant produced in an average of 6 weeks.

*Growth rate*.—Moderate to high, an average of 5 months to produce a finished plant in a 13-cm container or larger.

Branch description:

*Shape*.—Moderately angled, 5-sided.

*Branch color*.—Young stems; N144C, mature stems; N144D, internodes; 145A, angled N144C, axils 186A.

*Branch size*.—An average of 7 mm in diameter and an average of 35.5 cm in length.

*Branch surface*.—Moderately glossy and densely covered with strigose hairs; an average of 2 mm in length and N155A in color.

*Branch number*.—Average of 5 main stems, 3 lateral branches per main stem.

*Internode length*.—An average of 5.9 cm in length.

*Branch aspect*.—Main stems; average of 25° to vertical, lateral branches; average of 20° to main stems.

*Branch strength*.—Strong.

*Branching*.—Freely branching from base with lateral stems.

Foliage description:

*Leaf shape*.—Elliptic-obovate to obovate.

*Leaf division*.—Simple.

*Leaf base*.—Long cuneate.

*Leaf apex*.—Rounded to broadly bluntly acute.

*Leaf venation*.—Pinnate, color; upper surface a blend of NN155D and 157D, lower surface 144B.

*Leaf margins*.—Entire to coarsely very shallow serrate, non-undulate to coarsely slightly undulate.

*Leaf attachment*.—Petiolate.

*Leaf arrangement*.—Alternate.

*Leaf size*.—Average of 15.4 cm in length and 4.7 cm in width.

*Leaf color*.—Young upper surface; a blend of 144A and 146B, base of main vein NN155D, young lower surface; 138B, main vein 144A, mature upper surface; a blend of 137C and 147B, mature lower surface; 138B.

*Leaf surface*.—Both surfaces matte, very rough to the touch, densely pubescent with short strigose hairs; an average of 1 mm in length and N155A in color.

*Petioles*.—Average of 6 mm in length, flattened, average diameter at widest point 1 cm and at narrowest point 4 mm, upper and lower surface color; 145C, both surfaces slightly glossy and densely covered with strigose hairs; an average of 2 mm in length and N155A in color.

Flower description:

*Inflorescence type*.—Terminal capitulum, consisting of ray florets and disc florets.

*Capitulum number*.—Average of 7 per stem, 75 per plant.

*Lastingness of inflorescence*.—Average of 2 weeks, persistent.

*Capitulum size*.—Average of 3.8 cm in height, 9.5 cm in diameter, disc 2.5 cm in diameter.

*Fragrance*.—None.

*Involucral bracts* (*phyllaries*).—Cuneate base, bluntly acute apex, narrow oblong in shape, margins revolute, average of 28 arranged in 2 rows, rotate, held in an outward angle of 25° to horizontal, 2.3 cm in length and 5 mm in width, color; upper surface when fully open 137B, lower surface when fully open 137C, upper surface is matte, lower surface is slightly glossy, all surfaces including margins are moderately covered with strigose hairs; an average of 2 mm in length and N155A in color.

*Receptacle*.—Ovate in shape, an average of 8 mm in height, 7 mm in diameter, 157B, base N155D in color.

*Buds*.—Shape; semi-spherical, immature ray florets bend upwards, 2 cm in length, 4.4 cm in width, color; immature ray florets 12A, with a slightly darker tinge on the lower 1/3$^{rd}$ 21A, disc N144D, fading lighter towards the center 145C, immature involucral bracts 146B, densely covered with strigose hairs, on immature ray florets hairs on lower surface adpressed, 1 mm in length, 151D in color, absent on upper surface, on immature involucral bracts, 2 mm in length, NN155D in color.

*Peduncle*.—Strong, straight on top of main flowering stem, average of 15 cm in length and 4 mm in diameter, color; 144A and 144B, surface moderately glossy and densely covered with short strigose hairs; an average of 2 mm in length and N155A in color.

*Ray florets*.—Average of 14, rotate around the disc in 1 row, oblong to narrow elliptic in shape, average of 4.3 cm in length and 1.5 cm in width, praemorse apex, cuneate base, entire margins, both surfaces are glabrous and velvety, densely covered with very short hairs; 0.1 mm in length and 16A in color, held mostly vertical and varying angles between −25° and 25°, color; when opening upper surface 12A, lower 1/3$^{rd}$ 21A, when opening lower surface 151B, disc 138B, when fully open upper surface 14A, lower 1/3$^{rd}$ a blend of N163B and 163C, veins 144C, when fully open lower surface 14B.

*Disc florets*.—Average of 800, 12 whorls arranged spirally on a conical receptacle, lower 90% fused into tube, tubular, upright, 9 mm in length and 4 mm in width, free lobes have entire margins, apices of free lobes acute and curled backwards, both surfaces glabrous, slightly glossy, color; when opening upper and lower surface NN155D, upper half N186B, when fully open upper and lower surface NN155D, upper 1/3$^{rd}$ N186B, no spines, but a single bract is placed beside each disc floret; 1 per disc floret, flattened, an average of 7 mm in length and 1 mm in diameter, oblanceolate in shape, acute apex, narrowly cuneate base, color; apex 187A, mid-section 187B, base NN155B, matte surface and moderately pubescent on the apex with hairs; an average of 1 mm in length, 187B in color.

Reproductive organs (present on disc florets only):

*Gynoecium*.—Pistil; 1, 7 mm in length, style; 5.5 mm in length, color; NN155A, tip 203B, stigma; cleft, decurrent, 3.5 mm in diameter, 203B in color, ovary; 197C in color.

*Androecium*.—Stamens; 5, filaments; 1 mm in length, NN155D in color, anther; narrow oblong in shape, 3 mm in length, 0.5 mm in width, 187A in color, pollen; moderate in quantity and 15A in color.

*Fruit/seed*.—None observed to date.

It is claimed:

1. A new and distinct cultivar of *Rudbeckia* plant named 'RUDBKS772' substantially as herein illustrated and described.

* * * * *